(12) United States Patent
Paoletti

(10) Patent No.: US 7,225,598 B2
(45) Date of Patent: Jun. 5, 2007

(54) ALERT MEDICATION SAFETY SEAL SYSTEM AND METHOD

(76) Inventor: Richard D. Paoletti, 153 Owenwood Dr., Lincoln University, PA (US) 19352

( * ) Notice: Subject to any disclaimer, the term of this patent is extended or adjusted under 35 U.S.C. 154(b) by 386 days.

(21) Appl. No.: 10/632,191

(22) Filed: Jul. 30, 2003

(65) Prior Publication Data

US 2005/0023173 A1  Feb. 3, 2005

(51) Int. Cl.
*B65B 11/00* (2006.01)
*B65B 53/02* (2006.01)

(52) U.S. Cl. .............................. 53/397; 53/412; 53/447; 206/807

(58) Field of Classification Search ................ 53/397, 53/411, 412, 442; 206/807
See application file for complete search history.

(56) References Cited

U.S. PATENT DOCUMENTS

| | | | | |
|---|---|---|---|---|
| 3,826,059 A | * | 7/1974 | Novitch ....................... | 53/412 |
| 4,633,648 A | * | 1/1987 | Yeung ......................... | 53/412 |
| 4,641,362 A | * | 2/1987 | Muller ........................ | 383/115 |
| 4,724,973 A | * | 2/1988 | Shah ........................... | 53/442 |
| 4,976,798 A | * | 12/1990 | Hoffman ...................... | 53/442 |
| 5,000,804 A | * | 3/1991 | Nugent ........................ | 53/442 |
| 5,205,827 A | * | 4/1993 | Novacek et al. ............. | 604/110 |
| 5,292,018 A | * | 3/1994 | Travisano .................... | 215/246 |
| 5,495,944 A | * | 3/1996 | Lermer ....................... | 206/807 |
| 5,544,770 A | * | 8/1996 | Travisano .................... | 206/807 |
| 5,605,230 A | * | 2/1997 | Marino et al. ............... | 206/807 |
| 6,385,878 B1 | * | 5/2002 | Key ............................. | 40/306 |

* cited by examiner

*Primary Examiner*—Louis Huynh
(74) *Attorney, Agent, or Firm*—Anderson Kill & Olick, P.C.

(57) ABSTRACT

The present invention provides for method and system in which a heat-shrinkable plastic cover is placed over an individual conventional medicine container. The cover is heat shrunk around the container to form a tight-fitting seal which covers the majority of the original medication container. The seal must be opened in order to gain entry into an individual medication container just prior to the use or the administration of the product in the container. The seal includes an easy-open mechanism, such as a pull-tab or perforated tear strip. The purpose of the seal is to distinguish high-alert medications and requires an additional safety step in the medication administration process by requiring the removal of an additional cover which entirely encloses the container. The non-adhesive nature of the seal is significant in that the removal of the seal does not damage the original product labeling or leave unwanted residue on the medication container. The seal includes an integrated warning statement directed to point-of-use, high-alert medication preparations for the person preparing the medication for use. The level of repackaging would distinguish categories of high-alert medications, alerting users as to the classification of the medication. Application of the seal offers the user visual cues and "tactile awareness" different from the look and feel of the original container to distinguish high-alert medications from other medications.

16 Claims, 3 Drawing Sheets

ALERT MEDICATION SAFETY SEAL SYSTEM AND METHOD

BACKGROUND OF THE INVENTION

1. Field of the Invention

The present invention relates a method and improved alert system for medicine containers. In particular, the present invention relates to a method and improved alert system for medicine that when applied, will warn the preparer of the medication of the high risk nature of the pharmaceutical product and distinguish such medicine products with sound-alike and look-alike names.

2. Description of the Background Art

In preparing medication, the preparer needs to be alert for sound-alike and look-alike drug names and packages which can lead preparers such as physicians, pharmacists, nurses and other health care professionals to unintended interchanges of drugs which can result in patient injury or death. The existing medication-use system is flawed because its safety depends on human perfection. Simplicity, standardization, differentiation, lack of duplication and unambiguous communication are human factor concepts that are relevant to the medication-use process. These principles have often been ignored in drug naming, labeling, and packaging. Instead, current methods are based on long-standing commercial considerations and bureaucratic procedures. Although a variety of private-sector organizations have called for reforms in drug naming, labeling, and packaging standards, the problem remains.

Look-alike drug names and packages increase the risk of unintended interchanges of drugs that can result in serious complications, even death. Labels that are hard to read or confusing can also contribute to errors. Drug names appearing on labeling may be in small print. Two vials that appear to be virtually identical (except for the drug name) may contain vastly different drugs. If one of those vials contains a high-alert medication, the consequence of confusion could be tragic. One such example was recently printed in the Institute for Safe Medication Practices (ISMP) Medication Safety Alert Newsletter. In a pediatric ICU, a respiratory therapist removed a vial of sterile water to prepare a nebulizer treatment. As he pierced the vial, he realized the vial was actually Atracurium (a paralyzing agent). The 10 mL Atracurium (Bedford) and sterile water (Abbott) vials have similar purple color accents. Other mix-ups have been attributed to Bedford's atracurium and acetazolamide vials—both have red and white coloring with black print and are packaged in identical sized and shaped vials (see picture 1).

As a further example, Ketorolac and Atracurium are two different medicines with similar lavender labeling and gray snap-off caps (see picture 2). However, as Atracurium is a neuromuscular paralyzing agent, the danger of confusion between these two drugs is of great concern. This problem is discussed in the publication ISMP MEDICATION SAFETY ALERT! Vol. 8, Issue 1 (Jan. 19, 2003).

Another such example is Narcan and Norcuron, which both sound alike when ordered verbally and look alike when handwritten. Confusion between these two drugs can result in serious harm to a patient, as documented in the publication, ISMP MEDICATION SAFETY ALERT! Vol. 3, Issue 20 (Oct. 7, 1998). In that publication, it is noted that a pharmacist misheard a verbal order and dispensed Norcuron, a neuromuscular blocker, when in fact, Narcan was ordered. This resulted in the patient having a respiratory arrest and requiring intubation. Other situations are also documented in this article between these two drugs.

Heparin 10 unit vials and Heparin 10,000 unit vials are also confusingly similar in appearance. The difference in dosage of this blood thinner medication is dramatic and the wrong dosage can be harmful to a patient.

In view of the foregoing discussion, there is a need in the product packaging art for a method and a system that serves to differentiate high-alert medications from other medication products in similarly packaged containers.

SUMMARY OF THE INVENTION

The present invention avoids or substantially alleviates the aforementioned deficiencies associated with the prior art utilized in commercial packaging of high-alert medications.

The present invention provides for a method and system in which a heat-shrinkable plastic cover is placed over an individual conventional medicine container. The cover is heat shrunk around the container to form a tight-fitting seal which covers the majority of the original medication container. The seal must be opened in order to gain entry into an individual medication container just prior to the use or the administration of the product in the container. The seal includes an easy-open mechanism, such as a pull-tab or perforated tear strip. The purpose of the seal is to distinguish high-alert medications and requires an additional safety step in the medication administration process by requiring the removal of an additional cover which entirely encloses the container. The non-adhesive nature of the seal is significant in that the removal of the seal does not damage the original product labeling or leave unwanted residue on the medication container. The seal includes an integrated warning statement directed to point-of-use, high-alert medication preparations for the person preparing the medication for use. The level of repackaging would distinguish categories of high-alert medications, alerting users as to the classification of the medication. Application of the seal offers the user visual cues and "tactile awareness" different from the look and feel of the original container to distinguish high-alert medications from other medications.

The invention further comprises a heat-shrinkable plastic cover placed over an individual conventional medicine container. The seal is preferably adapted with a set of perforation lines. The perforations define lines of weakening which enable a user to quickly and easily remove the seal and gain access to the container's contents. Placement of the seal over the individual medication container extends over a portion of the medication container closure such that the closure may only be removed by first detaching the heat-shrinkable seal.

The seal contains both a warning statement and transparent portion which, when the seal is applied, allows viewing of the product labeling arranged on the exterior of the original medication container. More importantly, however, the warning statement and the distinguishing characteristics of the newly applied seal differentiate the product so that it may not be mistaken for a different product.

DETAILED DESCRIPTION OF THE PREFERRED EMBODIMENTS

Figure 1:
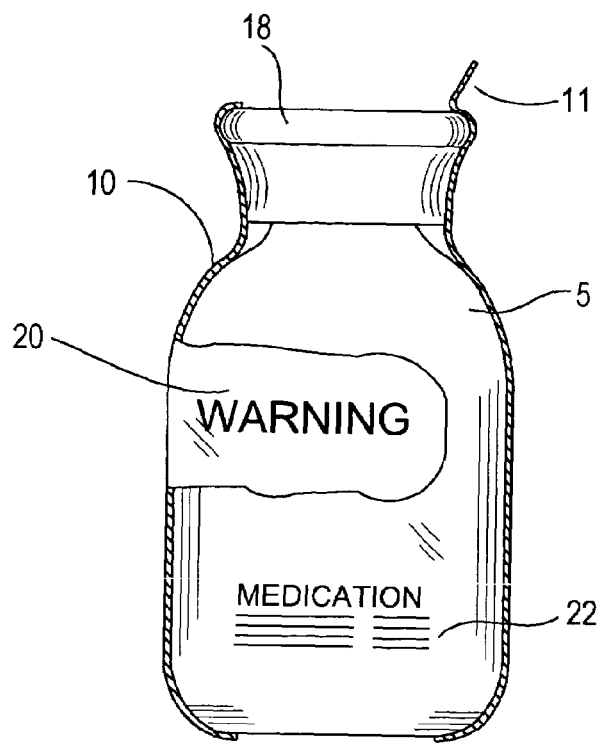
FIG. 1 illustrates a first embodiment of the invention showing the seal wrapped around a medicine container.
Figure 2:
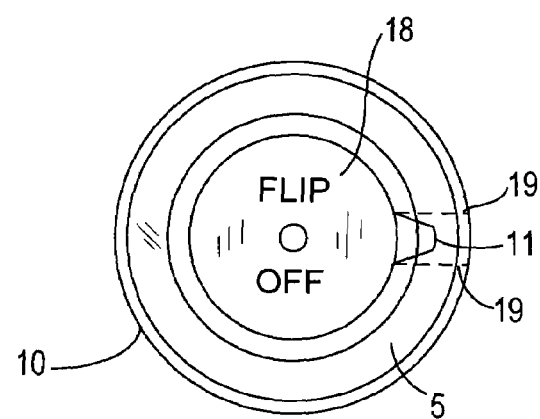
FIG. 2 is top view of FIG. 1.

Referring now to the drawings and, in particular, to FIG. 1. FIG. 1 shows a first embodiment of a medication bottle 5 having a heat shrink seal 10 of the present invention on it. The seal is preferably adapted with a set of perforation lines. The perforations define lines of weakening which enable a user to quickly and easily remove the seal and gain access to the container's contents. The seal 10 is placed over the individual medication container 5 so that extends over a portion of the medication container closure 18 (see FIG. 2) such that the closure 18 may only be removed by first detaching the heat-shrinkable seal 10. The seal does not require or have any adhesive material for affixing it to the medication container. This is advantageous because it does not result in adhesive residue on the medication container when the seal is removed from the medicine container and promotes the easy removal of the seal from the container. In addition, the seal 10 provides the user or preparer with tactile awareness as the seal 10 covering the cap of the medication container does not have a lip. Therefore, the lid of the container can only be felt if the seal 10 is removed.

Figure 3:
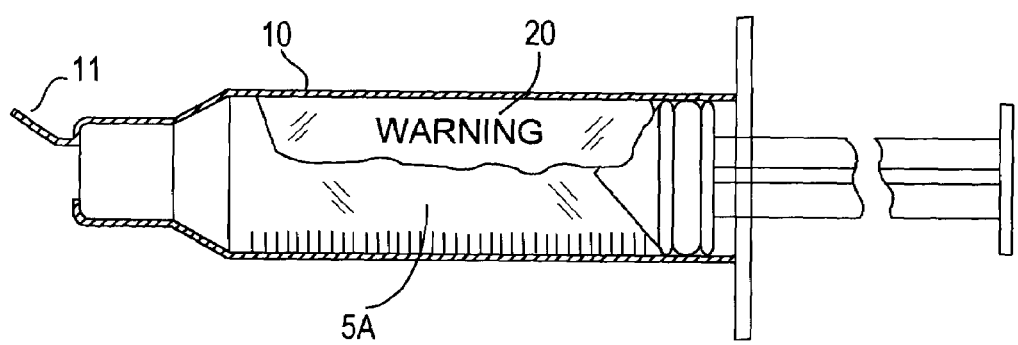
FIG. 3 is another embodiment of the invention in which the container is in the form of a syringe.
Figure 5:
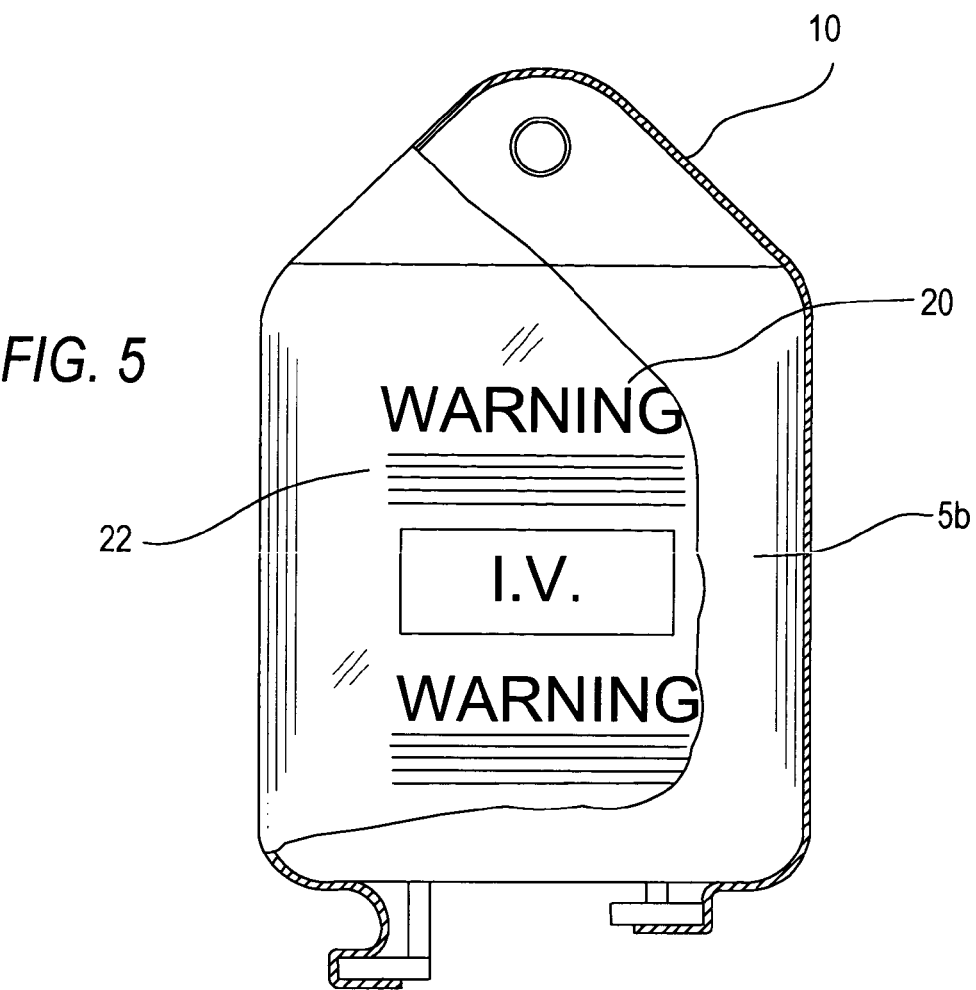
FIG. 5 is another embodiment of the invention in which the container is an intravenous bag.
Figure 6:
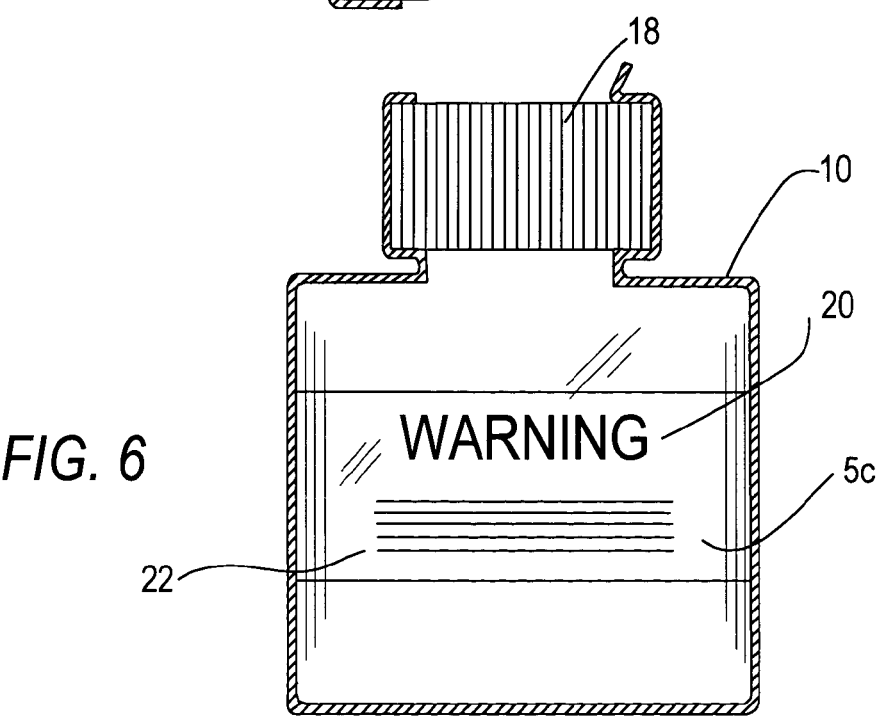
FIG. 6 is another embodiment of the invention in which the container is a vial.

The type of container can be of any configuration and embodiment such as in the form of a syringe type of container (5a) as shown in FIG. 3 or an intravenous (IV) bag (5b) as shown in FIG. 5. In addition, oral liquid pharmaceutical containers (see 5c in FIG. 6) can also utilize the seal mechanism and methodology of the present invention.

Figure 4:
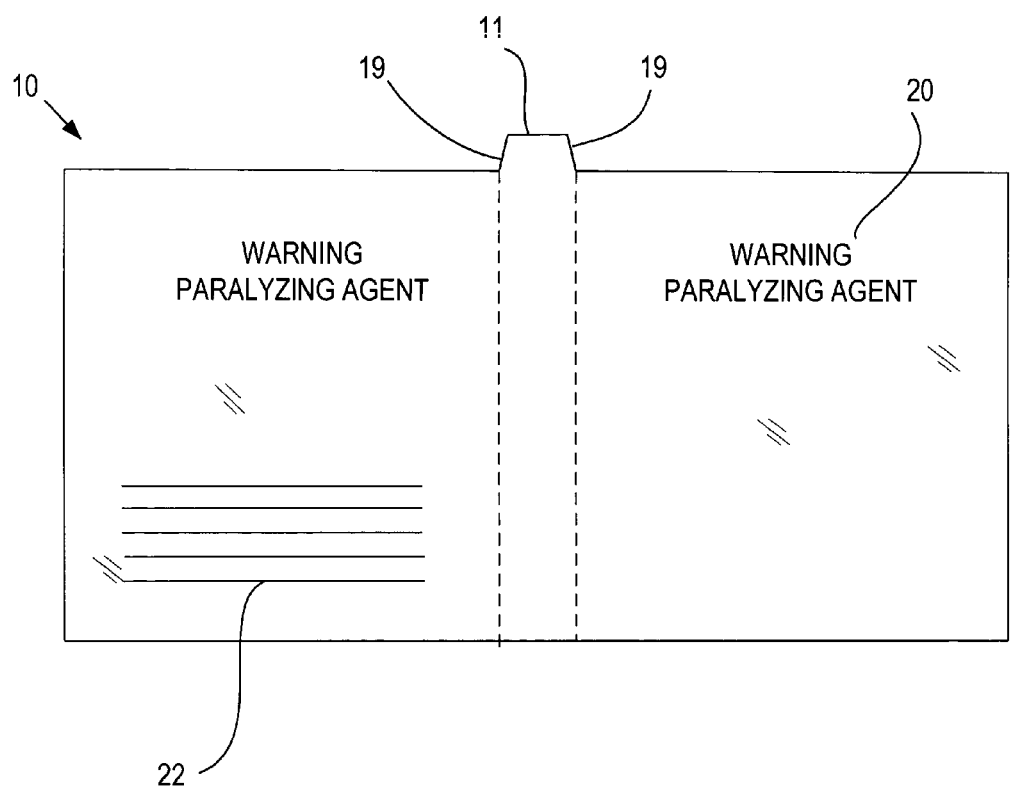
FIG. 4 shows the warning portion of the seal of the present invention.

FIG. 4 shows the seal 10 having a set of perforated lines 19 that define lines of weakening in the seal and permits a user to easily and quickly remove the seal and gain access to the container's (5, 5a) contents. A user pulls the seal off along the set of perforated lines 19 and removes the seal from the container 5, 5a. The set of perforated lines can be provided with the seal as either a pull tab or perforated tear strip. The seal further includes a warning label 20 with indicia and other symbols 22 directing the preparer to the point of use, high risk medical preparation for this medicine container. The warning indicia and symbols 22 provide visual cues and tactile awareness different from the look and feel of the original container to distinguish the container's high alert medications from other medications. Tactile awareness is provided to the preparer or user because the preparer or user will not feel the pull tab until the seal 10 is removed. In this way, the preparer of the high risk medication container will be alerted to distinguish this medication from other sound-alike and look-alike drug names and packages that can lead medical staff and other health care professionals to unintended interchanges of drugs that can result in injury or death to the patient. The fact that the warning statement is integral with the seal provides assurance that the preparer will not open the container without first reading the warning statement on the seal.

The present invention can also be employed for any IV bag prepared by hospital pharmacies containing a high alert medication. Traditionally, all IV bags prepared are commercially available. The only distinction between prepared products is the labeling, which typically contains only the drug name (warnings are optional). Even if a warning label is applied, the visual cue could be missed because it doesn't force action by the preparer such as removing a protective seal as is required with the present invention.

Different types of insulin (several different types of insulin are manufactured by a single company that use the same vial size, coloring, labeling specs, etc.) are easily confused during preparation. The present invention provides for color-coding overwraps detailing the type of insulin so that the preparer would be able to distinguish the products. The warning on the medication container of the present invention can be any of the following:

The generic statement "High Alert! Medication" could be used to distinguish any product alerting the user to the potential dangers of the drug and preventing a misadventure. This statement is suggested by the ISMP, but does not appear on any commercial packaging.

"Paralyzing Agent", is currently displayed on one commercial product. The additional warnings provided by the present invention warn the preparer to not use this product in a patient that is not intubated. This warning statement also alerts the preparer to the potential for respiratory depression. Many nurses do not know administration of paralyzing agents is prohibited in non-intubated patients and serious consequences may emerge.

"Concentrate" can be used to distinguish any high risk concentrated form of a medication. For example, both Heparin 10 and Heparin 10,000 units are packaged in small brown capped vials. A thousand-fold overdose is significant and has occurred in many hospitals. Therefore, the higher concentration could be 'protected' by providing an additional warning overwrap seal. "Concentrate" warnings are not utilized in commercially prepared products with the exception of potassium chloride. (See picture 3, brown capped vials).

"Note Preparation Instructions". Certain dry-powder medication vials are labeled as a dose but contain additional drug product in powder form. After the preparer reconstitutes the drug from powdered form, he may be led to believe that he does not have to measure the final solution and may inject the entire vial contents. This could result in an overdose. This is described in detail with reference to the drug Geodon in the publication ISMP MEDICATION SAFETY ALERT! Vol. 7, Issue 21 (Oct. 16, 2002).

Accordingly, the present invention provides for a greater degree of safety and control when a medication is being prepared or administered to ensure the wrong medication or wrong dosage of a high risk medication is not administered to a patient.

While presently preferred embodiments have been described for purposes of the disclosure, numerous changes in the arrangement of method steps and apparatus parts can be made by those skilled in the art. Such changes are encompassed within the spirit of the invention as defined by the appended claims.

The invention claimed is:

1. A safety seal method for maintaining high alert medications sealed prior to use or administration, the method comprising:

providing an individual high alert medication container having a body and a closure thereon, said body includes side wall and a base transversely connected to the side wall of the body, said closure includes a cylindrical wall and a top transversely connected to said cylindrical wall of the closure;

providing a transparent tubular heat-shrink plastic cover having a warning statement and other distinguishing characteristics thereon for the purpose of alerting a person preparing said high alert medication container from being mistaken for a different medication container, and a set of perforation lines;

placing said transparent tubular heat-shrink plastic cover over the individual high alert medication container; and applying heat to shrink the transparent tubular heat-shrink plastic cover to form a heat-shrunk plastic seal covering the individual high alert medication container including a portion of the base of the body and extending to include a portion of the top of the closure, wherein the set of perforation lines extends from a top edge of said heat-shrunk plastic seal located on the top of the closure to a bottom edge of said heat-shrunk plastic seal located on said base of said body; and completely removing of the entire heat-shrunk plastic seal from the individual high alert medication container prior to use or administration via the set of perforation lines.

2. The safety seal method according to claim 1 further comprising configuring said seal and said set of perforated lines as a pull tab.

3. The safety seal method according to claim 2 further comprising configuring said medicine container is configured as a bottle shaped container.

4. The safety seal method according to claim 3 further comprising providing tactile awareness of the seal being in place as the pull tab cannot be tactilely identified as separate from the seal until the seal is removed.

5. The safety seal method according to claim 1 further comprising configuring said seal and said set of perforated lines as a perforated tear strip.

6. The safety seal method according to claim 1 wherein said warning statement includes visual cues and tactile awareness distinguishing said medicine container's high alert medication from other medications.

7. The safety seal method according to claim 6 further comprising providing tactile awareness of the seal being in place as the seal is without a lip and the seal covers a lip of the medicine container.

8. The safety seal method according to claim 1 further comprising configuring said medicine container as a vial.

9. A safety seal system for maintaining high alert medications sealed prior to use or administration, comprising:

an individual high alert medication container having a body and a closure thereon, said body includes side wall and a base transversely connected to the side wall of the body, said closure includes a cylindrical wall and a top transversely connected to said cylindrical wall of the closure;

a transparent tubular heat-shrink plastic cover having a warning statement and other distinguishing characteristics thereon for the purpose of alerting a person preparing said high alert medication container from being mistaken for a different medication container, and a set of perforation lines;

said transparent tubular heat-shrink plastic cover being placed on said individual high alert medication container and heated to form a heat-shrunk plastic seal covering the individual high alert medication container including a portion of the base of the body and extending to include a portion of the top of the closure;

wherein the set of perforation lines extends from a top edge of said heat-shrunk plastic seal located on the top of the closure to a bottom edge of said heat-shrunk plastic seal located on said base of said body, and is configured for a complete removal of the entire heat-shrunk plastic seal from the individual high alert medication container.

10. The safety seal system according to claim 9 wherein said seal and said set of perforated lines are configured as a pull tab.

11. The safety seal system according to claim 10 wherein said pull tab cannot be tactilely identified as separate from the seal until the seal is removed thereby providing a user with tactile awareness of said seal being in place.

12. The safety seal system according to claim 9 wherein said seal and said set of perforated lines are configured as a perforated tear strip.

13. The safety seal system according to claim 9 wherein said warning statement includes visual cues and tactile awareness distinguishing said medicine container's high-alert medication from other medications.

14. The safety seal system according to claim 9 wherein said medicine container is configured as a bottle shaped container.

15. The safety seal system according to claim 14 wherein said seal is without a lip thereon and said seal covers a lip of the medicine container so that a user has tactile awareness of said seal being in place.

16. The safety seal system according to claim 9 wherein said medicine container is configured as a vial.

* * * * *